(12) United States Patent
Chikugo et al.

(10) Patent No.: US 7,475,717 B2
(45) Date of Patent: Jan. 13, 2009

(54) MOLD

(75) Inventors: Kazuyoshi Chikugo, Tokyo (JP);
Hidemi Ukai, Tokyo (JP); Koichi Murakami, Tokyo (JP); Koshichi Ogawa, Kanagawa (JP)

(73) Assignee: Ishikawajima-Harima Heavy Industries Co., Ltd., Tokyo (JP)

( * ) Notice: Subject to any disclaimer, the term of this patent is extended or adjusted under 35 U.S.C. 154(b) by 0 days.

(21) Appl. No.: 11/844,469

(22) Filed: Aug. 24, 2007

(65) Prior Publication Data

US 2007/0295470 A1  Dec. 27, 2007

Related U.S. Application Data

(62) Division of application No. 10/547,774, filed on Sep. 1, 2005, now Pat. No. 7,281,566.

(30) Foreign Application Priority Data

| Mar. 5, 2003 | (JP) | ............................ 2003-058713 |
| Jan. 30, 2004 | (JP) | ............................ 2004-023863 |
| Mar. 4, 2004 | (JP) | ................ PCT/JP2004/002708 |

(51) Int. Cl.
*B22C 9/04* (2006.01)
(52) U.S. Cl. ..................................... 164/361; 164/516
(58) Field of Classification Search ................. 164/361, 164/35, 45, 516
See application file for complete search history.

(56) References Cited

U.S. PATENT DOCUMENTS

| 3,074,151 A | | 1/1963 | Kroeckel |
| 4,355,428 A | * | 10/1982 | Deloison et al. ........... 623/23.5 |
| 4,600,546 A | | 7/1986 | Grundei |
| 5,016,702 A | * | 5/1991 | Ahlers ......................... 164/34 |
| 5,746,272 A | * | 5/1998 | Mastrorio et al. ........... 164/516 |

FOREIGN PATENT DOCUMENTS

| DE | 4106881 C1 | | 8/1992 |
| EP | 0834360 A1 | | 4/1998 |
| JP | 55-114439 | * | 9/1980 |
| JP | 55114439 A | | 9/1980 |
| JP | 10-155823 | | 6/1998 |
| JP | 11-33674 A | | 2/1999 |

* cited by examiner

*Primary Examiner*—Kuang Lin
(74) *Attorney, Agent, or Firm*—McCormick, Paulding & Huber LLP (57) ABSTRACT

A mold having a shell and a porous layer formed on the surface of the cavity of the shell. The mold can be suitably used for manufacturing a porous body having a porous layer on the surface thereof. The method for manufacturing the mold, includes the steps of forming a layer of combustible powdery particles around a wax mold, which is a lost pattern, a step of forming a film of a ceramic precursor slurry around the wax mold having powdery particles formed thereon, a step of subjecting the resultant product to a heat treatment, to thereby dewax the wax mold, and a step of firing the slurry film, to thereby burn and vanish the powdery particles in the slurry film and form a shell.

3 Claims, 8 Drawing Sheets

MOLD

CROSS-REFERENCE TO RELATED APPLICATIONS

This application is entitled to the benefit of International Application No. PCT/JP2004/002708 filed on Mar. 4, 2004, Japanese Patent Application No.2003-058713 filed on Mar. 5, 2003 and Japanese Patent Application No. 2004-023863 filed on Jan. 30, 2004 and is a Divisional application of U.S. Ser. No. 10/547,774, filed on Sep. 1, 2005, now U.S. Pat. No. 7,281,566.

FIELD OF THE INVENTION

The present invention relates to a mold used for an investment casting.

BACKGROUND OF THE INVENTION

In a carrier of a catalyst, or an artificial bone, an artificial dental root (hereinafter, referred to as an implant member) for artificial biomaterial transplantation, a porous layer having a porous structure is formed on the surface in order to increase a surface area.

As a method for forming a porous layer having a porous structure on a surface, the following two methods have been used, that is, (1) a method carrying out a laser beam machining on the surface of a metallic body (or an alloy body), and (2) a method piling up thin sheets made with metallic materials having many pores while three-dimensionally controlling a hole shape in the porous structure, which is described in Japanese Patent Application Laid-Open No. H10-155823.

Incidentally, as for the manufacturing method (1), although the metallic body (or the alloy body) having a porous structure only on the surface, that is, a rough surface, can be easily obtained, there was the problem that a porous layer having a three-dimensional porous structure cannot be obtained. Further, in the case of a metal (or an alloy) having high melting point, there were problems that a high output laser beam machine and a long processing time were necessary for the laser beam machining.

Further, as for the manufacturing method (2), although a porous layer having a three-dimensional porous structure could be formed, there were problems that it took the time and effort for controlling the pore shape and that a long time was necessary for manufacturing.

Thus, it is desired that the above-mentioned porous layer is made by a casting method capable of comparatively easy manufacture. When a porous article is manufactured by the casting method, projections formed on an inner surface of a mold constitute pores of a porous article. However, in order to take out a cast body from the mold, the head of each projection must be narrower than its base. Therefore, as for the pore shape of the porous article obtained by the casting method, a bottom part of the pore is narrower than an opening part of the hole. As a result, for example, one like a golf ball having a concave dimple on the surface could be cast, but there was a problem to make a cast article having a complicated three-dimensional porous structure on the surface by casting.

The present invention solves the above-mentioned problems, and the primary objective is to provide a method for manufacturing a mold, wherein a porous body can be made.

DISCLOSURE OF THE INVENTION

One embodiment of the present invention is as follows. That is, a layer of combustible powdery particles is formed around a wax mold, which is a lost pattern. A film of a ceramic precursor slurry is coated around the wax mold having a layer of powdery particles formed thereon. Then, a resultant product is heated to dewax the wax mold, and thereafter, the slurry film is fired to burn and vanish the powdery particles inside the slurry film, and to form a shell. Thereby, the mold having a porous layer on the surface of the cavity of the shell can be made, wherein the porous layer has a three-dimensional porous structure.

Another embodiment of the present invention is as follows. That is, a layer of combustible powdery particles is formed on an inner surface of a female mold for forming a wax mold, which is a lost pattern. A wax material is injected into the female mold, and the wax mold is formed around which has the layer of the powdery particles. Then, a film of a ceramic precursor slurry is coated around the wax mold. Then, after dewaxing the wax mold by heating, the powdery particles inside of the slurry film is burned and vanished by firing the slurry film, and a shell is formed. Thereby, the mold having a porous layer on the surface of the cavity of the shell can be manufactured, wherein the porous layer has a three-dimensional porous structure.

Another embodiment of the present invention is a mold made by any one of the above-described methods for manufacturing the mold, and the mold has a porous layer on the surface of the cavity of a shell, wherein the porous layer has a three-dimensional porous structure.

In addition, another embodiment of the present invention is a method for manufacturing a cast article by the steps of pouring a molten metal into the cavity of a mold obtained by any one of the above-described methods for manufacturing the mold, cooling the molten metal, and removing the shell. Thereby, it is possible to manufacture a cast article having a porous layer at least on the surface thereof, wherein the porous layer has a three-dimensional porous structure.

Furthermore, another embodiment of the present invention is a cast article manufactured by any one of the above-described methods. Thereby, it is possible to manufacture the cast article having a porous layer at least on the surface thereof, wherein the porous layer has a three-dimensional porous structure, and preferably to manufacture an implant member, a catalyst carrier, a turbine rotor, a turbine blade, or the like.

DETAILED DESCRIPTION OF PREFERRED EMBODIMENT

The present invention is described more extensively with attached drawings.

Figure 1:
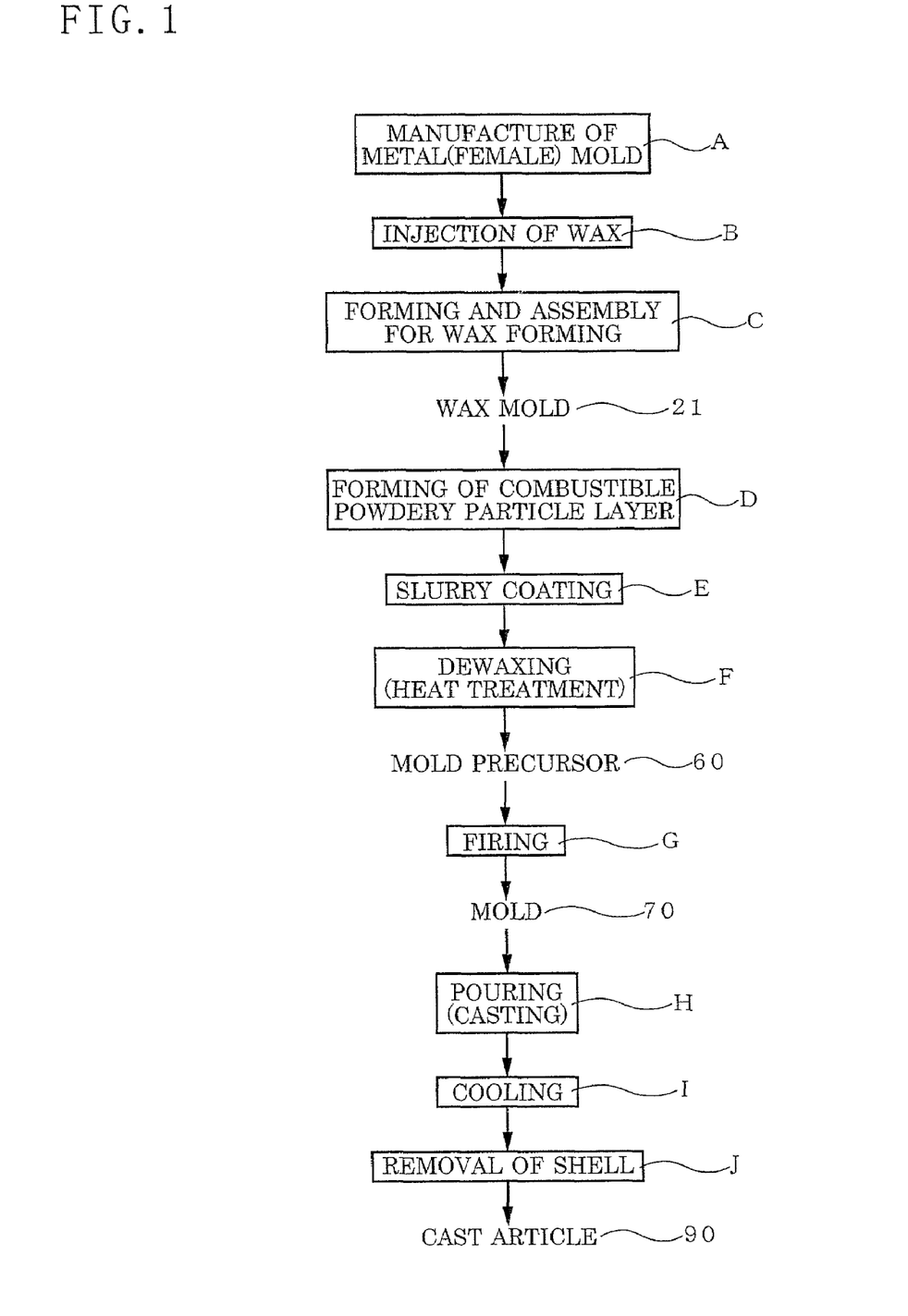
FIG. 1 is a flow chart showing a casting method of a cast article according to one preferred embodiment of the present invention.

FIG. 1 illustrates a flow chart of a casting method of a cast article according to one preferred embodiment of the present invention.

As illustrated in FIG. 1, the casting method of the cast article according to the present preferred embodiment uses an investment casting method (a lost wax method).

Figure 2:
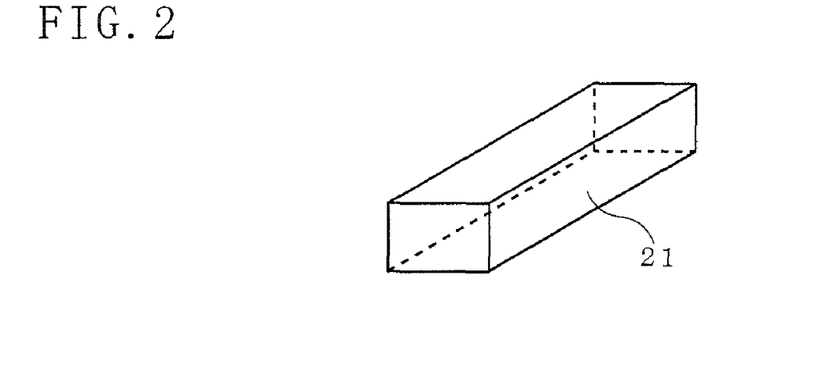
FIG. 2 is a perspective schematic view illustrating one example of a wax mold.

The method comprises steps of first manufacturing a metallic mold (a female mold) having a cavity with a predetermined shape (Process A), pouring a wax material into the metallic mold by a method such as an injection molding or the like (Process B), and taking out a wax molding body from the metallic mold after hardening the wax material (Process C). A wax mold (a male mold) 21, which is a lost pattern as illustrated in FIG. 2, can be obtained using the wax molding body. During the processes A to C, two kinds or more of wax molding bodies may be formed if necessary, to thereby obtain the desired wax mold 21 by assembling those. The wax mold 21 comprises an ingate, a runner and a sprue, which are used in the below-described casting although not illustrated in the drawings. Further, a plurality of wax molds may be integrated into a tree shape or a cluster shape. The wax material in this case includes not only waxes themselves but also whole resins (plastics).

Figure 3:
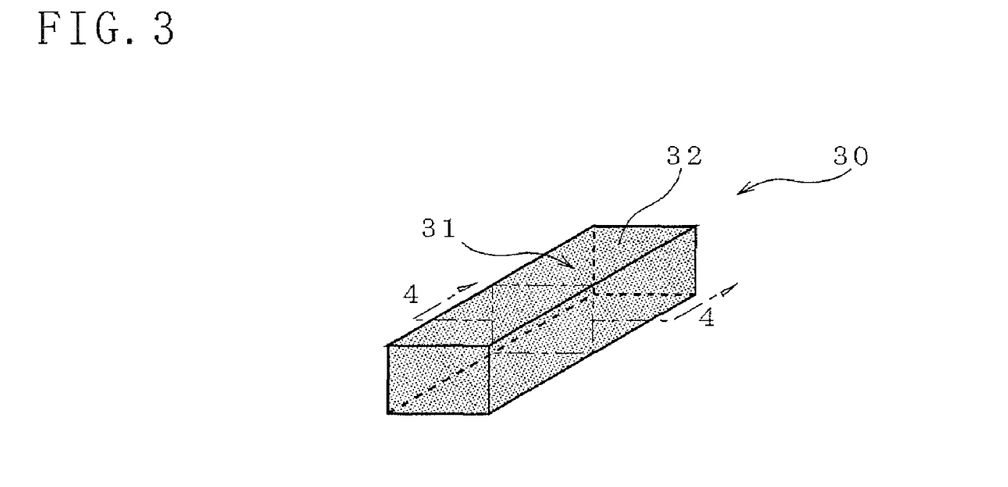
FIG. 3 is a perspective schematic view of a wax mold where a layer of combustible powdery particles is formed around the wax mold shown in FIG. 2.
Figure 4:
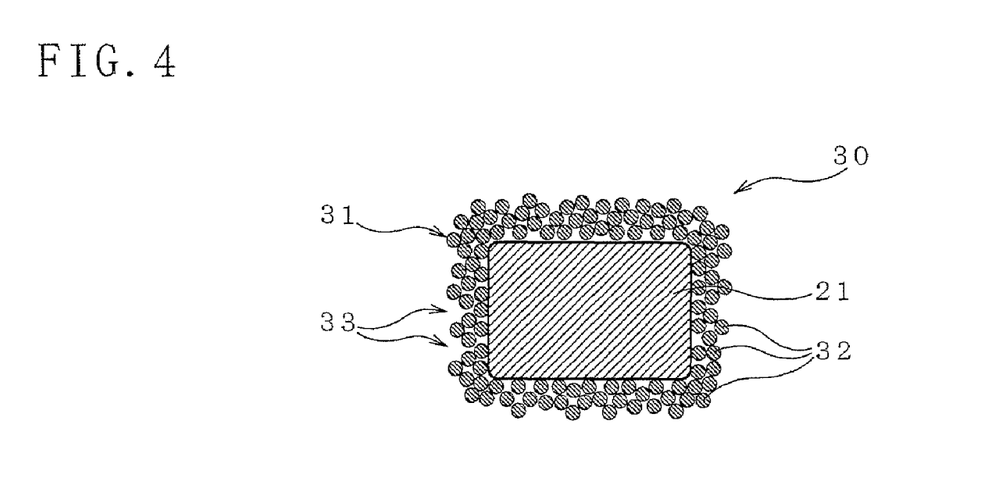
FIG. 4 is a cross-sectional view taken along the line 4-4 shown in FIG. 3.

Then, as illustrated in FIG. 3, a layer 31 consisting of many combustible powdery particles 32 is formed at a desired part around the wax mold 21 (Process D). Preferably, as illustrated in FIG. 4 as a cross sectional diagram which is taken along the line 4-4 in FIG. 3, many powdery or granular combustible powdery particles 32 are adhered at a part around the mold wax 21, wherein the part is desired to have a three-dimensional porous structure. Thereby, it is possible to obtain a wax mold 30 having the layer 31 formed around thereon, wherein the layer 31 has a three-dimensional porous structure 33.

At this time, it is possible to obtain the porous structure 33 whose pores are arranged randomly, or the porous structure 33 whose pores are aligned in a predetermined direction, by controlling an arrangement of each powdery particle 32 adhered around the wax mold 21. Further, the pore size and shape of the porous structure 33 can be controlled by changing the size and shape of the powdery particles 32. Furthermore, the thickness of a porous layer 74 of a mold 70 as described below, that is, the thickness of a porous layer 94 of a cast article 90 can be controlled by controlling the thickness of the layer 31.

Figure 5:
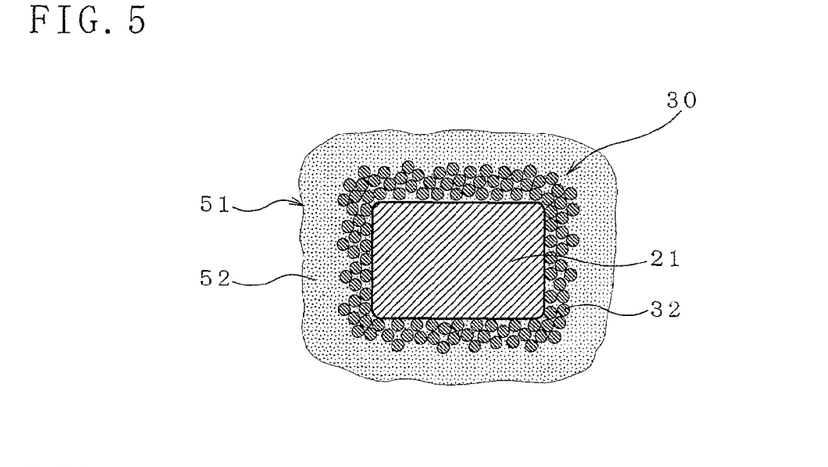
FIG. 5 is a cross-sectional view when a film of ceramic precursor slurry is coated around the wax mold shown in FIG. 4.

Then, as illustrated in FIG. 5, after a film of a ceramic precursor slurry 52 is adhered around the wax mold 30, the slurry 52 is dried, and then, a slurry film 51 is coated around the wax mold 30 (Process E). At this time, the slurry 52 also enters into a part of the porous structure 33 of the layer 31, that is, enters into a void space of the layer 31, and all the powdery particles 32 are covered with the slurry film 51. As a method for adhering the slurry 52, a dipping method, a spraying method, or a coating method can be used, but the dipping method is preferable since it has sufficient permeability of the slurry 52 to the inside of the layer 31. Further, the film thickness of the slurry film 51 is controlled so as to have a desired thickness by repeating operations of adhering and drying of the slurry 52.

Figure 6:
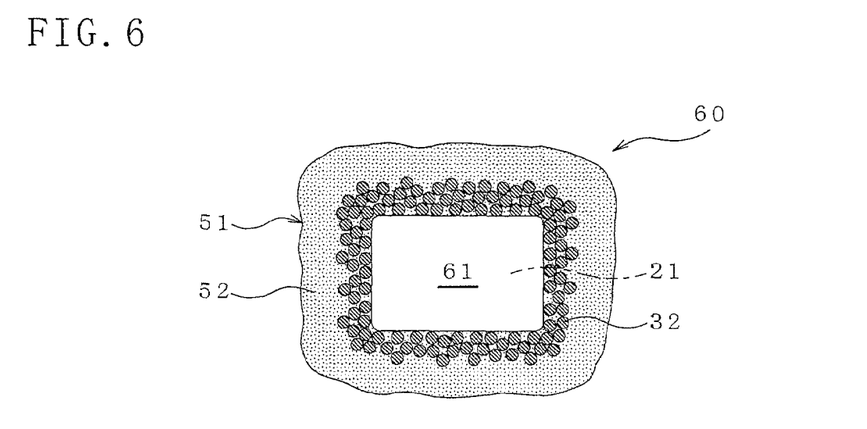
FIG. 6 is a cross-sectional view of a mold precursor obtained by dewaxing the wax from the coated wax mold shown in FIG. 5.

The wax mold 30 having the slurry film 51 coated thereon is subjected to a heat and pressure treatment at 4 to 8 atmospheres and at 100 to 180° C., preferably at 140 to 160° C., to thereby dewax the wax mold (Process F). Thereby, as illustrated in FIG. 6, the wax material is melted, and the wax mold 21 is lost to become a cavity 61, to thereby obtain a mold precursor (a mold preformed body) 60 having the cavity 61 inside the slurry film 51. In this process, each powdery particle 32 inside the slurry film 51 does not vanish but remains, and the shape of each powdery particle 32 (the layer 31) is kept.

Figure 7:
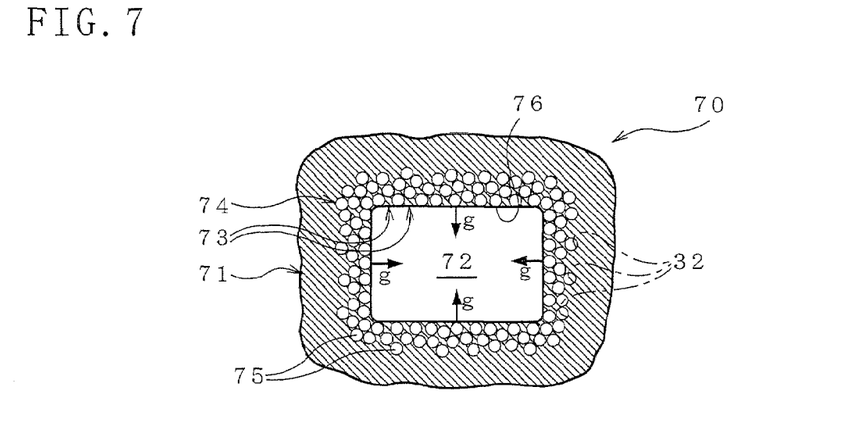
FIG. 7 is a cross-sectional view of a mold obtained by a firing treatment to the mold precursor shown in FIG. 6.

After dewaxing, the mold precursor 60 is subjected to a firing treatment at a temperature of 900 to 1,300° C. (Process G), and as illustrated in FIG. 7, the slurry film 51 is fired to be hardened to form a shell 71. In the firing treatment, each combustible powdery particle 32 remaining in the mold precursor 60 is burned and vanished gradually from a side facing to the cavity 61 toward the inner side of the mold precursor 60, before forming the shell 71. A portion occupied by each powdery particle 32 becomes a fine void space 75 by this burning. A gas g generated while burning a certain powdery particle 32 reaches to the cavity 61 of the mold precursor 60 passing through the adjacent fine void space 75, and then exhausted to the outside of the mold precursor 60. As for the burning and vanishing temperature of the powdery particles 32, the particle material is selected so that the temperature is not more than the firing temperature of the slurry film 51, preferably lower than the firing temperature of the slurry film 51 by 90° C. or more, and more preferably lower than the firing temperature of the slurry film 51 by 100° C. or more. As a result, when each powdery particle 32 is burned and vanished, it is unlikely that the fine void space 75 is damaged by the generated gas g. Thus, the shape of the fine void space 75 can be kept, and the fine void spaces 75 link each other. Thereby, as illustrated in FIG. 7, it is possible to obtain the mold 70 made of ceramics having a cavity 72 inside the shell 71, wherein the cavity 72 is comprised of the cavity 61 having the same shape as the wax mold 21 and a group of the fine void space 75 having the same shape as each powdery particle 32 (the layer 31). That is, the mold 70 has the porous layer 74 on the surface 76 of the cavity of the shell 71, wherein the porous layer 74 has a three-dimensional porous structure 73.

Figure 8:
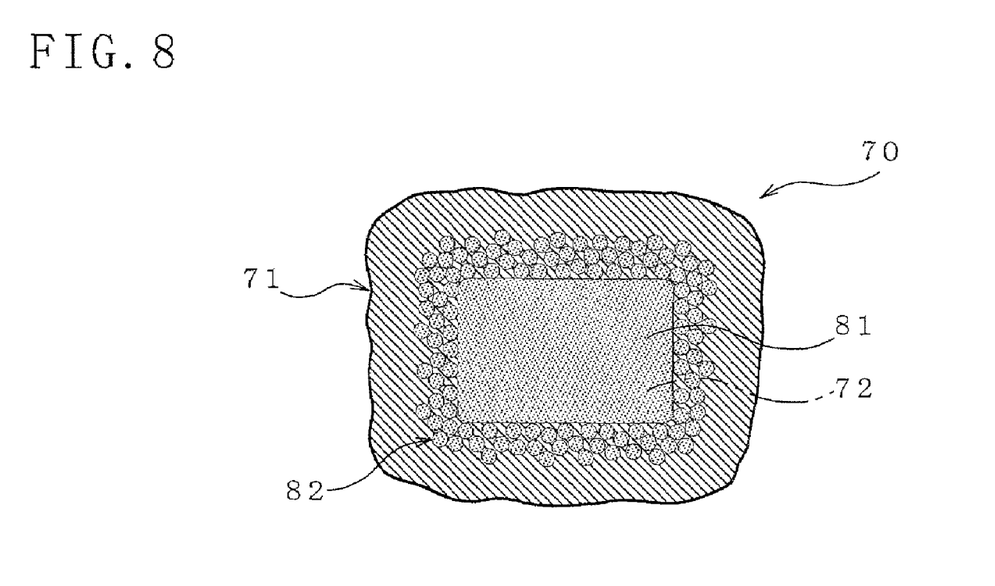
FIG. 8 is a cross-sectional view when a molten metal is poured into the mold shown in FIG. 7.

Then, as illustrated in FIG. 8, a molten metal 81 is poured into the cavity 72 of the mold 70 to be cast (Process H). At this time, since each fine void space 75 links one another, the molten metal 81 enters into up to every hole and corner of each fine void space 75. Then, the molten metal 81 is cooled (Process I) and then, the casting is completed. Thereby, a cast body 82 is formed in the mold 70. As a method for casting the molten metal 81, a pouring casting method, a centrifugal casting method, a suction casting method (low pressure casting), or the like can be applicable.

Figure 9:
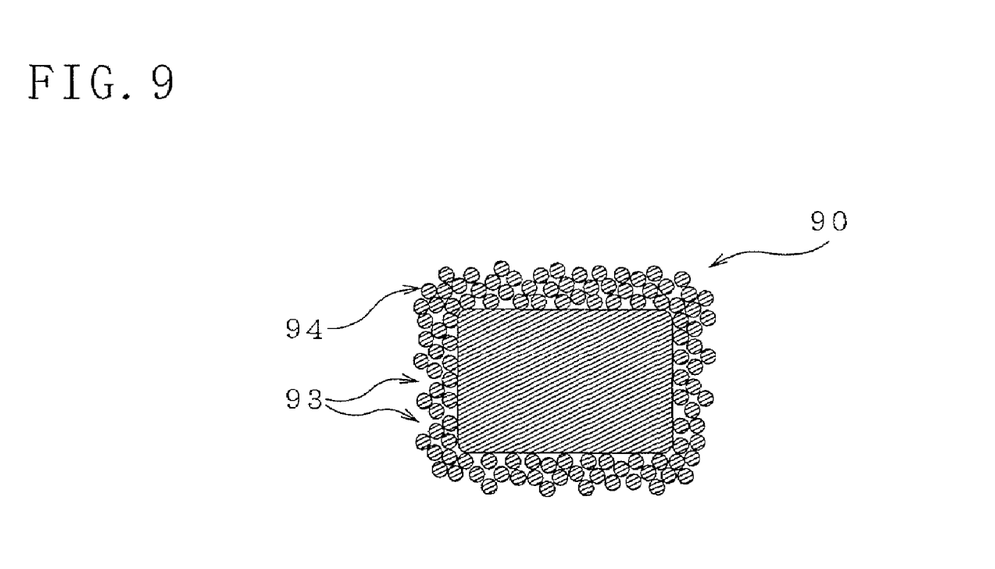
FIG. 9 is a cross-sectional view of a cast article according to one preferred embodiment of the present invention.

After the casting, the shell 71 is subjected to blast cleaning to remove the shell 71 (Process J). Thereby, as illustrated in FIG. 9, a cast article 90 as an integrated article having a porous layer 94 at least on the surface thereof can be obtained, wherein the porous layer 94 has a three-dimensional porous structure 93. As the method of the blast cleaning, any one of a sand blast method, a shot blast method, and a water jet method (spraying of high-pressure water) may be used. Further, as a method for removing the shell 71 other than the blast cleaning, a shakeout method can be used.

In this case, as a matrix of the powdery or granular combustible powdery particles 32, it is not especially limited if it can be completely (or substantially completely) burned and vanished at the temperature of the firing treatment of 900 to 1,300° C. For example, wood, fiber, carbon (graphite) or the like can be used. Further, as a method for adhering many powdery particles 32 around the wax mold 21, it is not especially limited, and for example, a method for coating an adhesive or a cohesive agent around the wax mold 21 can be used. At this time, if the adhesive or the cohesive agent is adhered around the powder particle 32 excessively, the fine void space 75 cannot be formed with sufficient accuracy, so that it is not preferable.

The matrix of the molten metal 81 is not especially limited if it is generally used as a metal (or an alloy) for casting. However, as the matrix, an alloy having a relatively high melting point, such as a Ti-based alloy, a Co-based alloy, a Ni-based alloy and an Al-based alloy, is preferable, and the Ti-based alloy, the Co-based alloy, and the Ni-based alloy, which are used for precision casting, are especially preferable as these alloys.

As described above, according to the casting method of the present invention, by using the mold 70 having the porous layer 74 on the surface 76 of the cavity of the shell 71, wherein the porous layer 74 has the three-dimensional porous structure 73, the cast article 90 which could not be manufactured by the casting method heretofore, having the porous layer 94 on the surface thereof can be obtained, wherein the porous layer 94 has a complicated, three-dimensional porous structure 93. This cast article cannot be manufactured by the conventional method. That is, a porous body having the porous layer on the surface thereof can be obtained, wherein the porous layer has the three-dimensional porous structure. Further, the porous layer 94 in the cast article 90 can be integrally formed with a main body, and the cast article 90 can be easily manufactured.

Further, the cast article 90 manufactured by the casting method according to the present preferred embodiment can be applied to a member necessary for having a large surface area, such as a carrier of a catalyst, an implant member, or the like, a rotary member or a blade member for a jet engine or a gas turbine engine, or a honeycomb member, or the like. The cast article 90 can be easily manufactured for a short time, as compared with the conventional manufacturing method described above.

Particularly, when a carrier of a catalyst is cast and formed by the casting method according to the present preferred embodiment, since the carrier of the catalyst has a porous layer on the surface thereof, a large amount of catalysts can be supported as compared with the conventional carriers of catalysts. Further, when an implant member is cast and formed similarly, the implant member can be strongly combined with biomedical tissues since it has a porous layer on the surface thereof. Because it is generally required that the implant member has the porous layer on the surface thereof, and the cast article 90 obtained by the casing method according to the present preferred embodiment is suitable as the implant member. Furthermore, when a rotor or a blade of a turbine; for example, a rotary member or a blade member of a jet engine or a gas turbine engine is cast and formed similarly, since these members have a porous layer on the surface thereof, weights of these members can be reduced, and a large amount of bubble layers can be formed on the surface of each member. As a result, these bubbles exert a heat insulation effect, and thus the member can keep the sufficient high temperature strength even when it is a thin member, and the weight of the member can be reduced.

Further, when casting, since a core, which is not shown, is placed at an arbitrary part in the cavity 72 of the mold 70 according to the present preferred embodiment, which is illustrated in FIG. 7, a hollow part can be formed at an arbitrary part of the cast article 90. As a result, the weight of the cast article 90 can be reduced.

In addition, in the present preferred embodiment, the case of forming the wax molding body by using the metal mold is described, but it is not especially limited to the metal mold. As a mold for forming a wax molding body, any mold can be used if it is generally used for molding waxes, plastics or the like. For example, a plastic mold or a wooden mold may be used.

Then, the other preferred embodiment of the present invention is described with the drawings.

Figure 10:
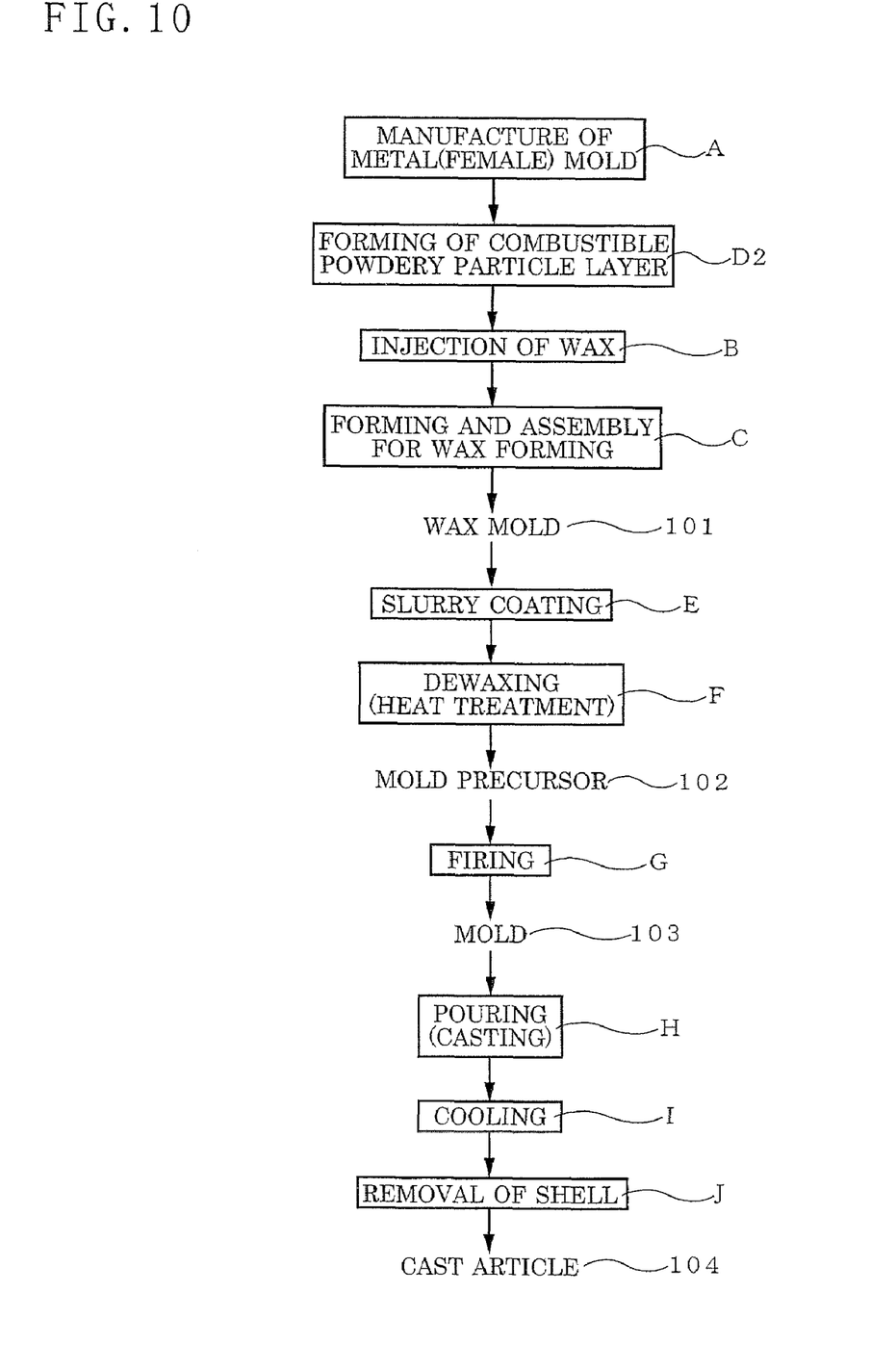
FIG. 10 is a flow chart showing a casting method of a cast article according to another preferred embodiment of the present invention.

A flow chart of the casting method of a cast article according to the other preferred embodiment of the present invention is shown in FIG. 10. In addition, the same codes as those of FIG. 1 are used in the same processes in FIG. 10.

Figure 11:
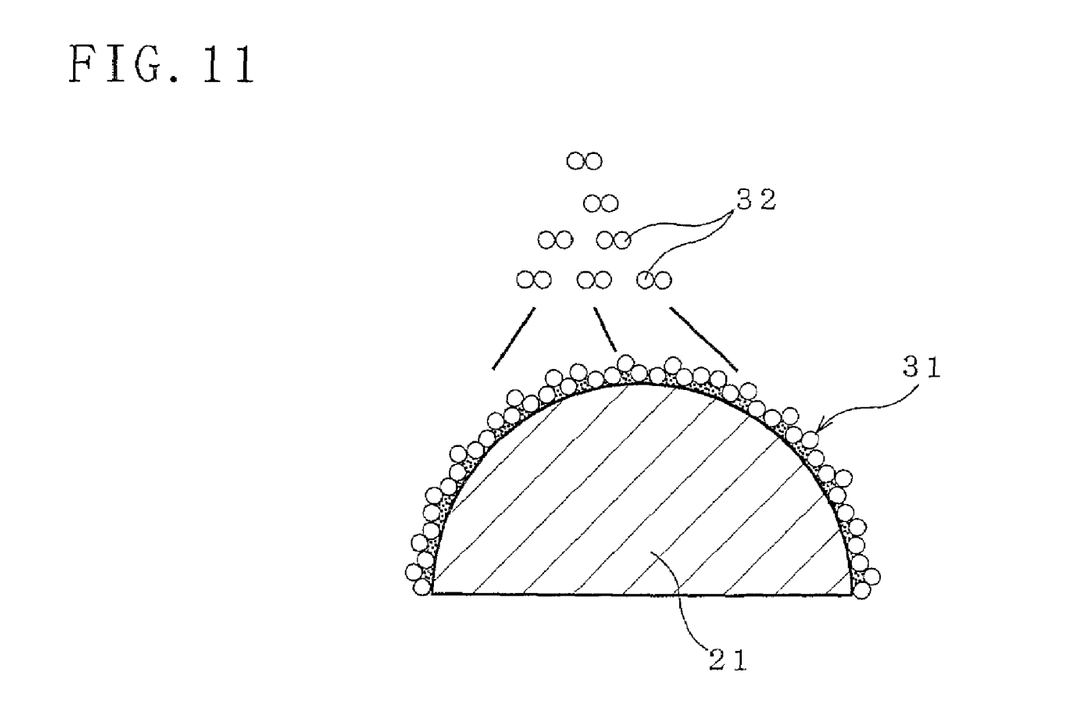
FIG. 11 is a cross-sectional schematic view for describing a process D shown in FIG. 1.

As illustrated in FIG. 11, the casting method according to the former preferred embodiment comprised the steps of forming the wax mold 21, randomly scattering many combustible powdery particles around the wax mold 21, and adhering and forming the layer 31 of the group of powdery particle 32 around the wax mold 21.

On the other hand, the casting method according to the present preferred embodiment is characterized by a step of adhering and forming a layer of a group of powdery particle on the inner surface of a metal mold for forming a wax mold.

Figure 12A:
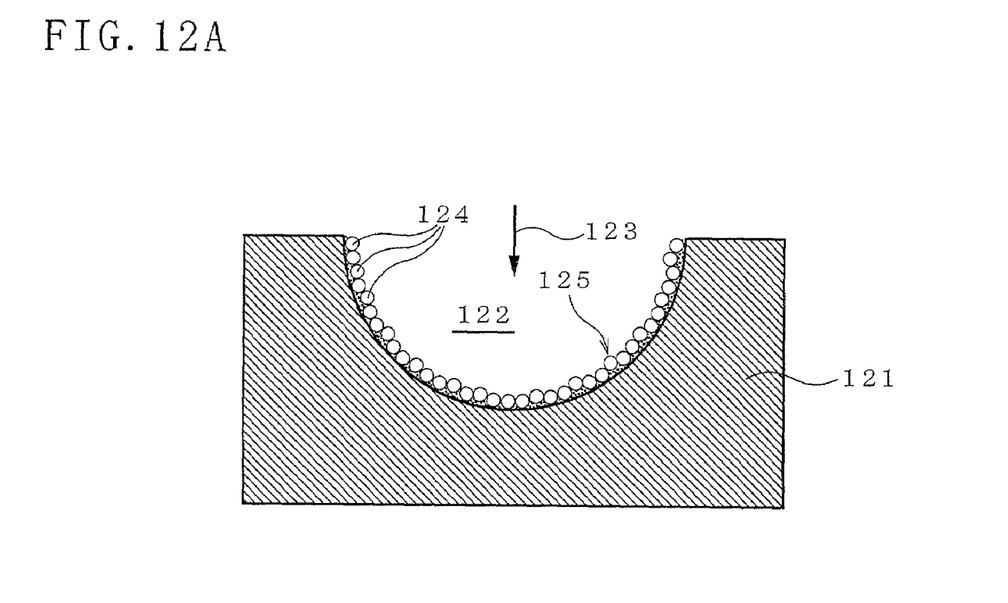
FIG. 12A is a cross-sectional schematic view for describing a process D2 shown in FIG. 10.

Specifically, a metal mold (a female mold) having a cavity with a predetermined shape is produced at first (Process A), as shown in FIG. 10. A layer of many combustible powdery particles is formed on the desired part of the inner surface of the metal mold (Process D2). For example, as illustrated in FIG. 12A, when a wax material 123 is injected into a cavity 122 of a metal mold 121, a layer 125 comprising many powdery or granular combustible powdery particles 124 is preformed, so as to be placed at a part on the inner surface of the metal mold 121, wherein the part is desired to have a three-dimensional porous structure. The layer 125 is preformed using an adhesion means (adhesives, mold lubricants, vaseline, lanolin or the like). The layer 125 may be formed as a plurality of layers if necessary. As the powdery particles 124, the same particles as the powdery particles 32 illustrated in FIG. 4 can be used.

Figure 12B:
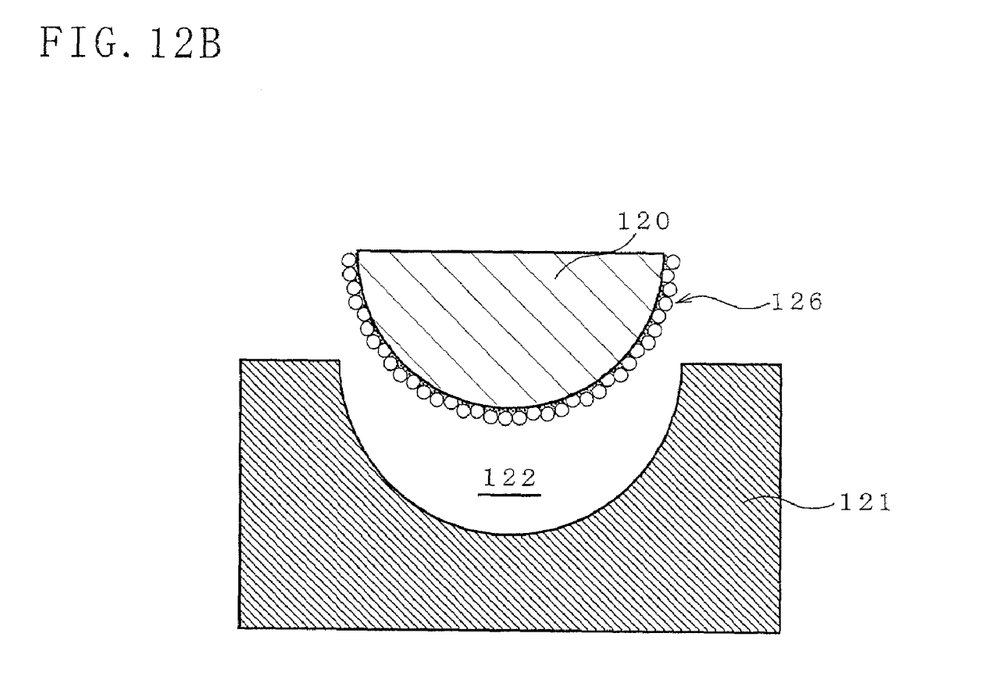
FIG. 12B is a cross-sectional schematic view when a wax molding body is taken out from a metallic mold in a process C shown in FIG. 10.

Then, the wax material (wax) 123 is poured into the cavity 122, or the wax material 123 is injected into the cavity 122 by the injection molding method or the like (Process B). After hardening the wax material 123, a wax molding body 120 is taken out from the metal mold 121 (Process C). As illustrated in FIG. 12B, the wax molding body 120 has a layer 126 on the surface thereof, wherein the layer 126 has a three-dimensional porous structure, and the outer surface of the layer 126 has no irregularities, that is, the height is approximately uniform, and the surface is smooth. By using this wax molding body 120, a wax mold (a male mold) 101, which is a lost pattern, can be obtained.

The desired wax mold 101 may be obtained by repeating the processes A, D2, B and C as needed to form two kinds or more of wax molding bodies, and by assembling them. The wax mold 101 comprises an ingate, a runner, and a sprue, which are used in the below-described casting although not illustrated in the drawings. Further, a plurality of wax molds 101 may be integrated into a tree shape or a cluster shape. The wax material in this case includes not only waxes themselves but also whole resins (plastics).

Then, the processes E and F are carried out for the wax mold 101 in the same procedure as that of the casting method according to the former preferred embodiment, to thereby obtain a mold precursor 102 having a void space in a slurry film. In this process, the powdery particles 124 do not vanish but remain in the slurry film, and the shape of each powdery particle 124 (layer 125) is kept.

Then, the process G is carried out for the mold precursor 102 in a similar procedure to that of the casting method according to the former preferred embodiment, to thereby obtain a mold 103 made of ceramics having a cavity inside the shell, wherein the cavity is comprised of a cavity having the same shape as the wax mold 101 and a group of the fine void space having the same shape as each powdery particle 124 (the layer 125). That is, the mold 103 has a porous layer on the surface of the cavity of the shell, wherein the porous layer has a three-dimensional porous structure having a substantially uniform depth.

Then, the processes H, I and J are carried out for the mold 103 in a similar procedure to that of the casting method according to the former preferred embodiment, to thereby obtain a cast article 104. The cast article 104 has a porous layer at least on the surface thereof, wherein the porous layer has a three-dimensional porous structure. The cast article 104 having the smooth outer surface of the porous layer is a comparatively flat integral body.

In the process D2, by controlling an arrangement of each powdery particle 124 adhered on the inner surface of the metal mold 121, it is possible to obtain the layer 125 having a porous structure whose pores are randomly arranged or a porous structure whose pores are aligned in a predetermined direction. Further, by changing the size and shape of the powdery particles 124, the pore size and pore shape of the layer 125 having the porous structure can be controlled. Furthermore, by controlling the thickness of the layer 125, the thickness of the porous layer of the mold 103, that is, the thickness of the porous layer of the cast article 104 can be controlled.

Further, in the process B, when the wax material 123 is poured, the temperature of the wax material 123 is controlled to be between the softening point or more and the melting point+30° C. or less. Thereby, the viscosity of the wax material 123 is controlled, and the wax material 123 does not reach to the surface of the metal mold 121 passing through the gap between the powdery particles 124 due to the surface tension of the wax material 123. Further, when the wax material 123 is injected by injection molding, the injection pressure is controlled to have a suitable value so that the wax material 123 does not reach to the surface of the metal mold 121 passing through the gap between the powdery particles 124.

Further, in the process C, when the wax molding body 120 is taken out from the metal mold 121, it can be taken out intact in most cases when mold lubricant, vaseline, lanolin, or the like is used as the adhesion means. Meanwhile, when the adhesive is used as the adhesion means, a peeling liquid for the adhesive is poured into the gap between the metal mold 121 and the wax molding body 120, to thereby take out the wax molding body 120 after the adhesive is peeled off.

Also in the casting method according to the present preferred embodiment, it is possible to obtain the similar working effect to that of the casting method according to the former preferred embodiment.

Further, as for the casting method according to the present preferred embodiment, since the layer 126 formed on the surface of the wax mold 101 is formed using the inner surface of the metal mold 121, the reproducibility of the layer 126 is favorable as compared with the casting method according to the former preferred embodiment, where the layer 31 is formed by randomly scattering many powdery particles 32 on the surface of the wax mold 21.

Further, as for the cast article 90 obtained by the casting method according to the former preferred embodiment, the outer surface (the outline) of the porous layer 94 having the three-dimensional porous structure 93 is not uniform and irregular. In this case, when an implant member using the cast article 90 is embedded (implanted) in biomedical tissues, the implant member may be caught by the biomedical tissues due to the ununiform and irregular outer surface of the porous layer 94. In order to prevent this problem, it is necessary that the surface of the porous layer 94 of the implant member (the cast article 90) is subjected to a machining to remove the irregularity in order to decrease the chance to be caught and to increase embeddability. As a result, although the outer surface of the porous layer 94 can be made uniform, a part of the porous structure 93 of the porous layer 94 of the cast article 90 must be scraped away. Thus, the utilization of the formed porous structure cannot be maximized.

As for the casting method according to the present preferred embodiment, when the wax mold 101, which is the lost pattern, is manufactured, the shape of the outer surface of the layer 125 becomes substantially equal to the shape of the inner surface of the metal mold 121 by pasting the layer 125 comprising the many powdery particles 124 on the inner surface of the metal mold 121 in advance. As a result, as for the wax molding body 120 obtained by pouring the wax material 123 into the metal mold 121, the outer surface of the layer 126 formed on the surface is substantially uniform and smooth. Thereby, also as for the cast article 104, which is finally obtained by using the wax mold 101, the outer surface of the porous layer having the porous structure is substantially uniform and smooth. Therefore, when an implant member is manufactured using the cast article 104, it is not necessary to perform machine processing on the outer surface of the porous layer of the implant member, and the implant member can be embedded without being caught just as it is manufactured (without processing). That is, the utilization of the porous structure of the porous layer of the cast article 104 can be maximized, and the manufacturing efficiency of the porous structure is favorable.

In the casting method according to the present preferred embodiment, described is the case where the layer 125 consisting of many powdery particles 124 is adhered and formed on the inner surface of the metal mold 121 for forming the wax mold 101 by the adhesion means. However, it is not especially limited to this case. For example, when the combustible powdery particles 124 constituting the layer 125, which is preformed on the inner surface of the metal mold 121, are magnetic particles, the layer 125 can be formed on the inner surface of the metal mold 121 by only applying a magnetic field to the metal mold 121. In this case, the wax molding body 120 is taken out from the metal mold 121 by only the steps for pouring the wax material 123, hardening it, and stopping the application of the magnetic field to the metal mold 121. Thus, the wax molding body 120 can be easily taken out.

As described above, the present invention is not limited to the above-described preferred embodiments, and needless to say, various embodiments can be considered in addition to the above-preferred embodiments.

Hereinafter, the present invention is described on the basis of examples, but it is not limited to these examples.

EXAMPLE 1

Wax was poured at 80° C. into a metal mold having a cavity with a predetermined shape. After hardening the wax, a pattern (a wax molding body) was taken out from the metal mold. The wax molding body thus obtained was shaped to have a tree shape, to thereby manufacture a wax mold.

A spray paste was sprayed onto a part of the wax mold, wherein the part was desired to be porous, and many wood pieces having sizes of approximately 0.5 to 1.0 mm were scattered and adhered on the part sprayed with the spray paste. This work was repeated as appropriate, to thereby form a porous layer having a porous structure, wherein the porous layer had many wood pieces piled up to have a plurality of layers.

Then, slurry for precision casting was coated on the wax mold having the porous layer, and it was dried for 3 hours or more, to thereby form a slurry film. This work was repeated 9 times in total.

Then, the wax mold was heated and pressurized at 140 to 150° C. and 5 to 6 atmospheres for 7 minutes to dewax the wax mold, to thereby obtain a wax precursor (a wax preformed body). Then, the wax precursor was subjected to a firing treatment at 1,100° C. for 2 hours, to thereby manufacture a mold consisting of a shell obtained by firing and hardening the slurry.

Then, the mold was preheated at 900° C., and a molten Co-based superalloy was poured into the cavity of the mold at a molten metal temperature of 1,500° C. to cast it. Then, the molten metal was cooled, to thereby manufacture a cast body in the mold.

Then, the mold was subjected to a sandblast treatment to remove the shell, to thereby manufacture a cast article.

Figure 13:
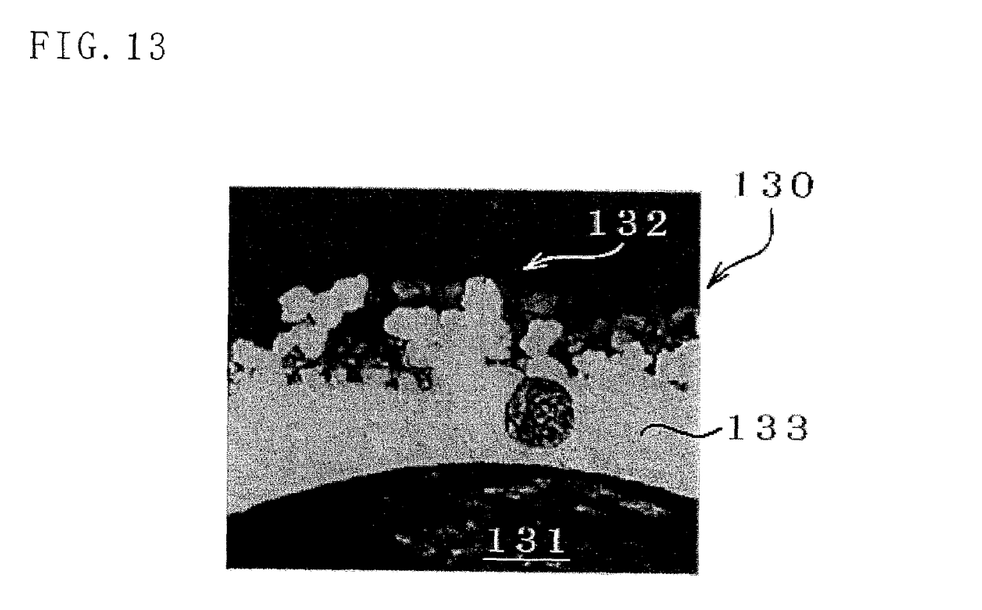
FIG. 13 is a cross-sectional observation view of a cast article obtained in Example 1.

As the cross-sectional observation view of the cast article is illustrated in FIG. 13, a cast article 130 had integrally a porous layer 133 at least on the surface of a main body 131, wherein the porous layer 133 had a three-dimensional porous structure 132. As for the porous layer 133, the height of the outer surface was not uniform and the outer surface was irregular.

EXAMPLE 2

Vaseline was coated on the inner surface of a metal mold having a cavity with a predetermined shape. Then, a spray paste was sprayed onto a part of the inner surface of the metal mold, wherein the part was desired to be porous, and many wood pieces having sizes of approximately 0.5 to 1.0 mm were scattered and adhered on the part sprayed with the spray paste. This work was repeated as appropriate, to thereby form a porous layer having a porous structure, wherein the porous layer had many wood pieces piled up to have a plurality of layers.

Then, a wax was poured into the metal mold at 80° C. After hardening the wax, a pattern (a wax molding body) was taken out from the metal mold. A wax molding body thus obtained was shaped to have a tree shape to thereby manufacture a wax mold.

A cast article was manufactured in a manner similar to Example 1 except for the use of this wax mold.

Figure 14:
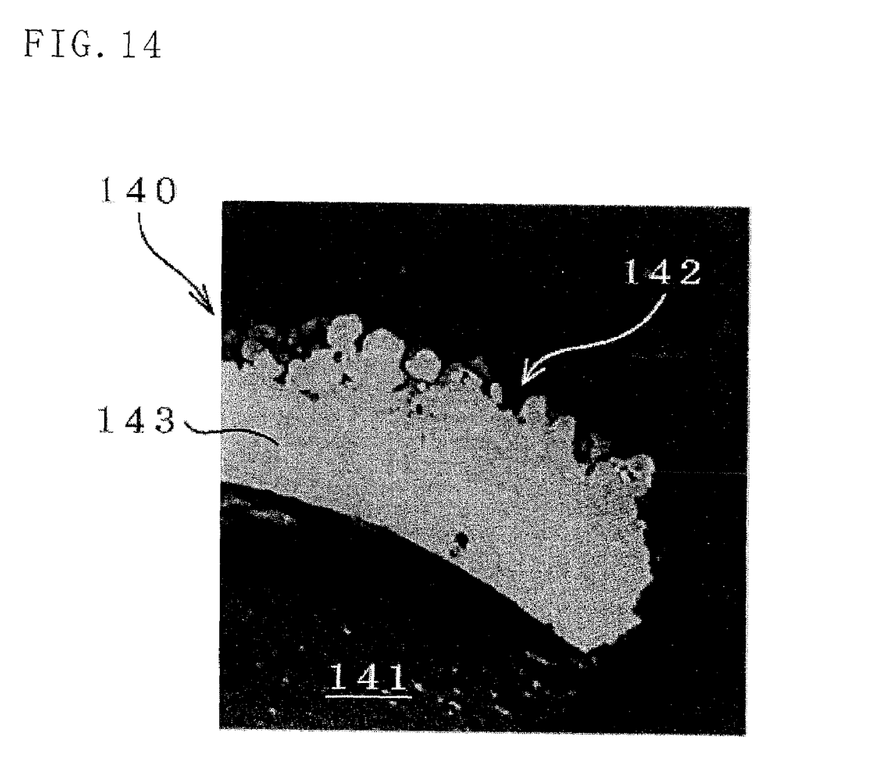
FIG. 14 is a cross-sectional observation view of a cast article obtained in Example 2.

As the cross-sectional observation view of the cast article is illustrated in FIG. 14, a cast article 140 had integrally a porous layer 143 at least on the surface of a main body 141, wherein the porous layer 143 had a three-dimensional porous structure 142. As for the porous layer 143, the height of the outer surface was uniform and the outer surface was not irregular.

EXAMPLE 3

As for the cast article 130 obtained in Example 1 and the cast article 140 obtained in Example 2, porosities of the porous layers 133 and 143 were compared.

As a result, the cast article 130 in Example 1 has 30% higher porosity in the porous layer 133 than that in the porous layer 143 of the cast article 140 in Example 2. Specifically, in the porous layer 133 of the cast article 130 in Example 1, the pore rate in a certain cross section was about 50%. On the other hand, in the porous layer 143 of the cast article 140 in Example 2, the pore rate in a certain cross section was about 35%. Due to an irregular height of the outer surface of the porous layer 133, the cast article 130 was considered to have higher porosity than that of the cast article 140 having a uniform height of the outer surface of the porous layer 143.

Further, in the cast articles 130 and 140 in Example 1 and Example 2, the depths of the porous layer from the uppermost surface to the deepest part were 2.08 mm and 1.96 mm, respectively, and these were considered to be substantially equal. That is, with respect to the depth of the porous layer, there was substantially no difference in both articles.

What is claimed is:

1. A mold, comprising a porous layer having a three-dimensional porous structure on a surface of a cavity of a shell, said mold being manufactured by the method comprising the steps of:
    scattering and adhering combustible powdery particles around a wax mold, which is a lost pattern, to thereby form a layer of combustible powdery particles around thereof, wherein said powdery particles have a particle size of from about 0.5 mm to about 1.0 mm;
    coating a film of a ceramic precursor slurry around the wax mold having the layer of the powdery particles formed thereon;
    subjecting the wax mold coated with the slurry film to a heat treatment at 100 to 180° C., to thereby dewax only the wax mold without said combustible powdery particles burning and vanishing; and
    firing the slurry film, to thereby burn and vanish the powdery particles in the slurry film and form said three-dimensional porous structure on said surface of said shell, wherein said three-dimensional porous structure includes a plurality of layers of pores, each pore having a size of from about 0.5 mm to about 1.0 mm; and
    wherein said porous structure has a depth extending from an uppermost surface to a lowermost surface of said porous structure, said depth being about 2 mm, and wherein said pores are continuous in a direction of said depth with adjacent pores being partly continuous, wherein said continuity of said pores in said depth direction being a result of said burning and vanishing of said powdery particles which turn to gas and exit said porous structure.

2. A mold manufactured according to claim 1 further comprising the steps of:
    burning and vanishing said powdery particles near the firing temperature of said slurry film.

3. A mold manufactured according to claim 1 further comprising the steps of:
    burning and vanishing said powdery particles at a temperature lower than the firing temperature of the slurry film by 90° C. or more.

* * * * *